(12) United States Patent
Buchbinder et al.

(10) Patent No.: US 9,743,967 B2
(45) Date of Patent: Aug. 29, 2017

(54) MANDIBULAR FIXATION PLATE

(71) Applicant: DePuy Synthes Products, Inc., Raynham, MA (US)

(72) Inventors: Daniel Buchbinder, Scarsdale, NY (US); Ross Jonathan Hamel, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 140 days.

(21) Appl. No.: 14/724,005

(22) Filed: May 28, 2015

(65) Prior Publication Data

US 2015/0257805 A1 Sep. 17, 2015

Related U.S. Application Data

(63) Continuation of application No. 12/963,725, filed on Dec. 9, 2010, now Pat. No. 9,066,767.

(60) Provisional application No. 61/285,781, filed on Dec. 11, 2009.

(51) Int. Cl.
*A61B 17/80* (2006.01)

(52) U.S. Cl.
CPC ...... *A61B 17/8071* (2013.01); *A61B 17/8057* (2013.01)

(58) Field of Classification Search
CPC .................................................. A61B 17/8071
See application file for complete search history.

(56) References Cited

U.S. PATENT DOCUMENTS

| | | | |
|---|---|---|---|
| 4,905,680 | A | 3/1990 | Tunc |
| 6,053,919 | A | 4/2000 | Talos et al. |
| 6,730,091 | B1 | 5/2004 | Pfefferle et al. |
| 6,960,211 | B1 | 11/2005 | Pfefferle et al. |
| 2001/0012940 | A1 | 8/2001 | Tunc |
| 2002/0183752 | A1 | 12/2002 | Steiner et al. |
| 2006/0235408 | A1 | 10/2006 | Wang et al. |
| 2007/0238069 | A1 | 10/2007 | Lovald et al. |
| 2008/0015593 | A1 | 1/2008 | Pfefferle et al. |
| 2008/0021452 | A1 | 1/2008 | Ducharme et al. |
| 2008/0161861 | A1 | 7/2008 | Huebner |

FOREIGN PATENT DOCUMENTS

| | | |
|---|---|---|
| CN | 1893885 A | 1/2007 |
| CN | 201223440 Y | 4/2009 |
| DE | 19834326 | 2/2000 |
| DE | 20007908 | 12/2000 |
| DE | 10125092 | 12/2001 |
| DE | 10 2004 01905 | 11/2005 |

(Continued)

OTHER PUBLICATIONS

"English Translation of German Patent DE 102004019059 filed Nov. 17, 2005, Applicant: Ebid Rainer", Morningside Translations, Aug. 21, 2013, 8 pages.

(Continued)

*Primary Examiner* — Christian Sevilla
(74) *Attorney, Agent, or Firm* — Baker & Hostetler LLP

(57) ABSTRACT

A bone fixation implant is provided that includes a bone fixation plate and a plurality of fasteners. The bone fixation plate corresponds generally to stress lines imparted onto the mandible during anatomical function of the mandible. Thus, the bone fixation plate includes a primary leg and an auxiliary leg extending obliquely out from the primary leg.

20 Claims, 7 Drawing Sheets

(56) References Cited

FOREIGN PATENT DOCUMENTS

| | | |
|---|---|---|
| EP | 2509524 B1 | 2/2014 |
| FR | 2622431 | 5/1989 |
| JP | 03-096811 | 10/1991 |
| JP | 2003-530138 | 10/2003 |
| JP | 2006-506140 | 2/2006 |
| JP | 2009-500093 | 1/2009 |
| WO | WO 2005/044122 | 5/2005 |
| WO | WO 2011/072107 | 6/2011 |

OTHER PUBLICATIONS

Feller et al., "Analysis of Complications in Fractures of the Mandibular Angle—A Study With Finite Element Computation and Evaluation of Data of 277 Patients", Journal of Cranio-Maxillofacial Surgery, Oct. 31, 2003, 290-295.

Lauer et al., "Transorable Operative Therapy Von Kiefergelenkfrakturen mit einer 3D-Platte", Mund Keifer GesichtsChir, Aug. 2006, 10, 335-340.

Luegmair et al., "Surgical Instrument of AO Type C Distal Humeral Fractures: Internal Fixation with a Y-Shaped Reconstruction (Lambda) Plate", Journal of Shoulder and Elbow Surgery, Jan.-Feb. 2008, 113-120.

Meyer et al., "Photoelastic Analysis of Bone Deformation in the Region of the Mandibular Condyle During Mastication", Journal of Cranio-Maxillofacial Surgery, Jun. 2002, 30(3), 160-169.

Meyer et al., "Development and Biomechanical Testing of a New Osteosynthesis Plate (TCP) Designed to Stabilize Mandibular Condyle Fractures", Journal of Cranio-Maxillofacial Surgery, Mar. 2007, 35(2), 84-90.

Meyer, "Radiusplate (Angle-Stable Dorsal Radial Plate) Mini Fragment", Konigsee Implantate Und Instrumente Zur Osteosynthese GmbH, Oct. 2006, 12 pages (with translation).

Meyer, "Analyse Photoelasticimetrique Des Deformations Osseuses De La Region Du Condyle Mandibulaire Lors De La Mastication", Thesis Pages, University Louis Pasteur, Strasbourg, Nov. 17, 2000, 6 pages (3 page English translation included).

Neff, Andreas, Christoff Pautke, and Hans-Henning Horch, "Traumatologie des Gesichtsschadels", Mund-Kiefer-Gesichtschirurgie 4, 2007, 88-91.

Tominaga et al., "Biomechanical Evaluation of Different Types of Rigid Internal Fixation Techniques for Subcondylar Fractures", Journal of Oral Maxillofacial Surgery, Oct. 2006, Issue 10, vol. 64, 1510-1516.

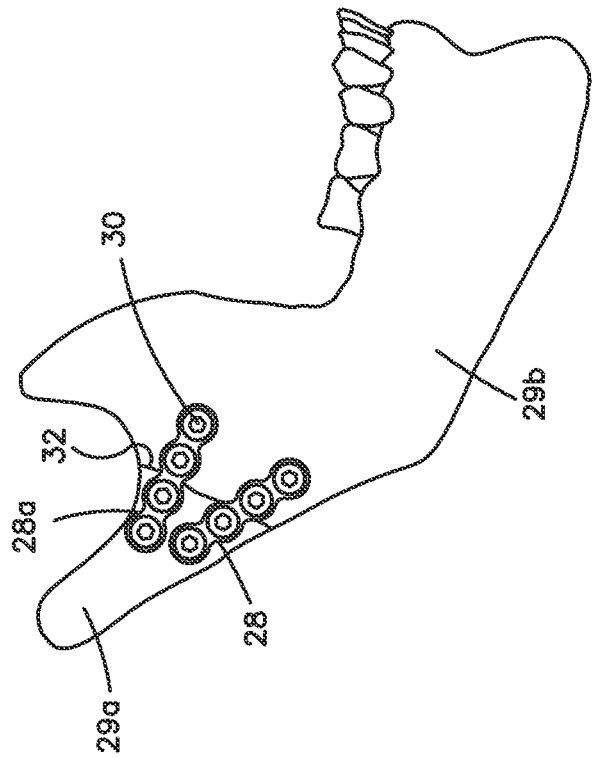
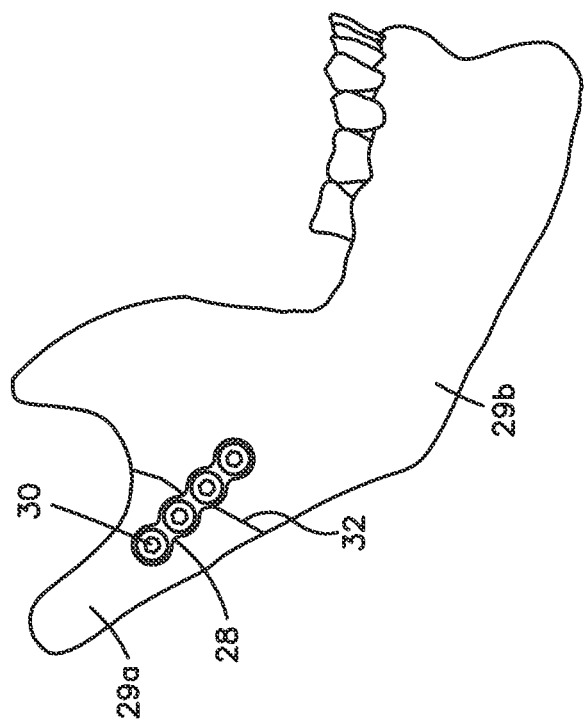

MANDIBULAR FIXATION PLATE

CROSS-REFERENCE TO RELATED APPLICATIONS

This application is a continuation of U.S. patent application Ser. No. 12/963,725, filed Dec. 9, 2010, which claims benefit to U.S. Provisional Patent Application Ser. No. 61/285,781, filed Dec. 11, 2009, the disclosures of which are hereby incorporated by reference as if set forth in their entireties herein.

TECHNICAL FIELD

The present disclosure relates generally to bone fixation implants, and in particular relates to a bone fixation implant configured to repair a mandibular fracture.

BACKGROUND

When bones are damaged through trauma or disease, bone fixation implants are commonly used to provide anatomical reduction of bone fragments, to maintain their position after reduction, and to ensure union in a desired position. Thus, bone fixation implants are typically designed to achieve proper anatomic fit and function.

Referring to FIGS. 1-2A, in which anatomical structure on the left side of a patient with the letter "L" and mandibular anatomy on the right side of the patient with the letter "R," a fractured mandible 20 defines a fracture site 32 that separates a pair of fractured bone segments 29a-b. Conventional approaches to fixation of a fractured mandible 20, for instance at the subcondylar region 22 (disposed between the condyle 24 and the ramus 26) include implanting a bone fixation plate 28 over the fracture site 32, and affixing the plate to the mandible 20, for instance using bone screws 30, to connect the fractured bone segments 29. The fracture site 32 in the subcondylar region 22 can be located anywhere between and including the upper subcondylar region 22a and the lower subcondylar region 22b.

Unfortunately, it has been found that the forces applied to the bone plate 28 during the anatomical function of the mandible 20 can adversely affect the ability of the bone plate 28 to ensure union of the bone fragments in their desired position. For instance, long narrow plates are susceptible to deformation in response to bending and twisting forces that applied to the plates by muscles such as the masseter, temporalis, and medial and lateral pterygoid.

Accordingly, as shown in FIG. 2B, another conventional approach is to add a second bone fixation plate 28A positioned adjacent the bone plate 28, such that each of the pair of plates absorb roughly half of the forces absorbed by the plate 28 alone. However, incorporating a second bone fixation plate adds cost and complexity to the surgical procedure. Yet another mandibular fixation approach includes affixing so-called three-dimensional fixation plates to the mandible 20. These fixation plates are more trapezoidal in shape than the long narrow bone plates 28, and are thus wider to better resist bending and twisting forces. However, since the wider geometry includes two side-by-side screw holes at the apex of the plate, the plates are limited regarding the height on the condyle 24 at which they are placed. Thus, the three-dimensional plates lack positional flexibility, and are difficult to implement when treating a fracture at the upper subcondylar region 22a.

SUMMARY

In accordance with one embodiment, a mandibular bone fixation plate is configured to be fixed to a mandible. The mandibular bone fixation plate includes a primary leg, and an auxiliary leg extending obliquely out from the primary leg, such that the primary leg generally corresponds in shape to a posterior border of a mandible, and the auxiliary leg generally corresponds in shape to a sigmoid notch of the mandible.

DESCRIPTION OF THE DRAWINGS

The foregoing summary, as well as the following detailed description, is better understood when read in conjunction with the appended drawings. For the purpose of illustrating a subcondylar fixation implant and related method thereof, there is shown in the drawings exemplary embodiments, in which like reference numerals correspond to like reference numerals throughout. The subcondylar fixation implant and related methods are not limited to the specific embodiments and methods disclosed, and reference is made to the claims for that purpose.

FIG. 2A is a perspective view of a conventional bone fixation plate attached to a pair of fractured subcondylar bone segments;

FIG. 2B is a perspective view of a pair of conventional bone fixation plates attached to a pair of fractured subcondylar bone segments;

DETAILED DESCRIPTION

The illustrated embodiments are directed to a bone fixation implant that may be implanted to facilitate proper union of two fractured bone segments. The fixation implant has particular utility as mandibular fixation implant having accurate anatomical shape and providing accurate anatomical fit.

Certain terminology may be used in the following description for convenience only and should not be considered as limiting in any way. For instance, a bone fixation implant 50 in accordance with one embodiment includes a bone fixation plate 52. The bone fixation plate 52 defines a plate body 51 that is elongate along a longitudinal direction L, further extends along a lateral direction A that is substantially perpendicular to the longitudinal direction L, and defines a thickness that extends in a transverse direction T that is substantially perpendicular to both the longitudinal direction L and the lateral direction A. As oriented in FIG. 3, the bone plate body 51 extends vertically along the longitudinal direction L, and generally horizontally along a lateral and transverse directions A and T. Accordingly, the bone fixation plate 52 is described herein in the orientation illustrated in FIG. 3, it being appreciated that the orientation of the bone fixation plate 52 can change during use. Accordingly, while certain terminology may be used in the following description, it should not be considered as limiting in any way.

Figure 3:
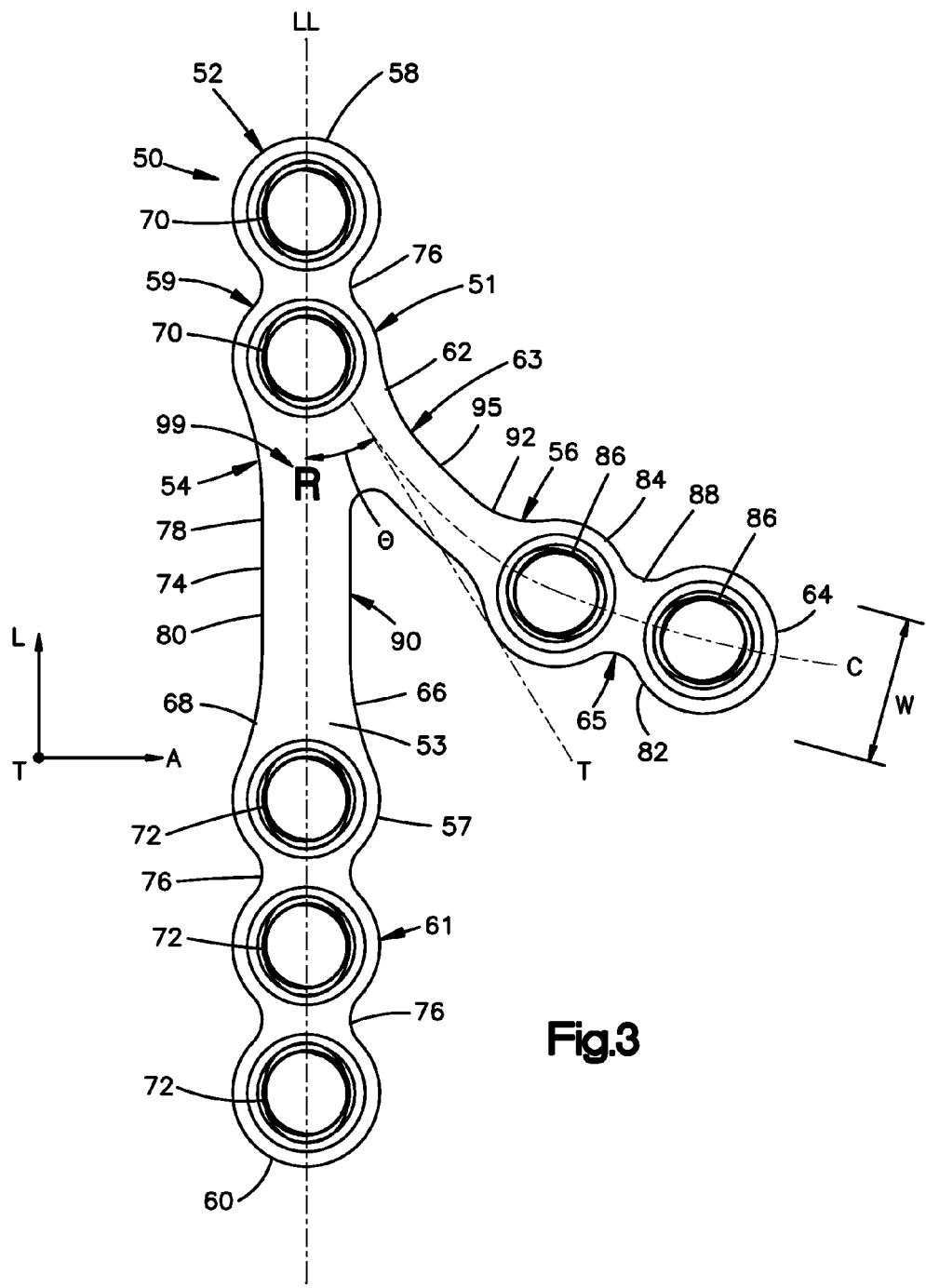
FIG. 3 is a top plan view of a subcondylar bone fixation plate constructed in accordance with one embodiment.

With continuing reference to FIG. 3, a bone fixation implant 50 constructed in accordance with one embodiment includes the bone fixation plate 52 and at least one bone fastener such as a plurality of bone fasteners 55 (see FIG. 4) configured to attach the fixation plate 52 to underlying bone structure. The bone fixation plate 52 defines a plate body 51 that includes a primary fixation leg 54 and an auxiliary fixation leg 56 that extends obliquely from the primary fixation leg 54. The primary leg 54 extends substantially longitudinally along a central longitudinal axis LL between a first proximal longitudinal end 58 and a second distal longitudinal end 60 spaced from the proximal longitudinal end 58 along the longitudinal direction L. The primary leg 54 can have a length of about 35 mm along the central longitudinal axis LL, though it should be appreciated that the length can be anywhere in the range of about 20 mm and about 45 mm. The bone fixation plate 52 and fasteners 55 can be constructed from implant grade titanium, though any suitable alternative material could be used as desired.

The plate body 51 further defines a plurality of transverse proximal bone fixation apertures 70 and distal bone fixation apertures 72 that extend through the primary leg 54 and are configured to receive respective permanent bone fasteners 55 (see FIG. 4), which can be provided as bone screws, rivets, pins, nails, or any suitable alternative fasteners, configured to attach the bone plate 52 to underlying bone structure permanently, that is for substantially as long as the bone plate 52 remains implanted. The bone fixation plate 52 defines a first outer surface 53 that receives the fasteners 55, and a transversely opposed bone-facing surface 57 that can face and abut the underlying bone when the fixation plate 52 is implanted onto underlying bone structure. Bone-facing surface 57 can be contoured to match the surface of the underlying bone structure. The bone fixation plate 52 can define a transverse thickness between the opposed surfaces 53 and 57 of about 1 mm, though it should be appreciated that the transverse thickness can be anywhere in the range of about 0.5 mm and 1.5 mm, or within any alternative range as desired.

In the illustrated embodiment, the apertures 70 and 72 define cylindrically shaped screw holes, and can be threaded or unthreaded as desired. In the illustrated embodiment, a pair of proximal longitudinally spaced apertures 70 is disposed at a proximal portion 59 of the primary leg 54 adjacent to the proximal end 58, and three distal longitudinally spaced apertures 72 are disposed at a distal portion 61 of the leg 54 that is disposed adjacent to the distal end 60. Thus, the distal end 60 has a longitudinal length greater than that of the proximal end 58. The adjacent proximal apertures 70 are spaced apart the same distance as the adjacent distal apertures 72, though it should be appreciated that the spacing between adjacent apertures 70 and 72 could differ as desired. It should be further appreciated that the number of apertures 70 and 72 at the proximal and distal portions 59 and 61, respectively, could differ as desired, though the plate body 51 defines more apertures 72 at the distal portion 61 of the primary leg 54 than apertures 70 at the primary portion 59.

Figure 1B:
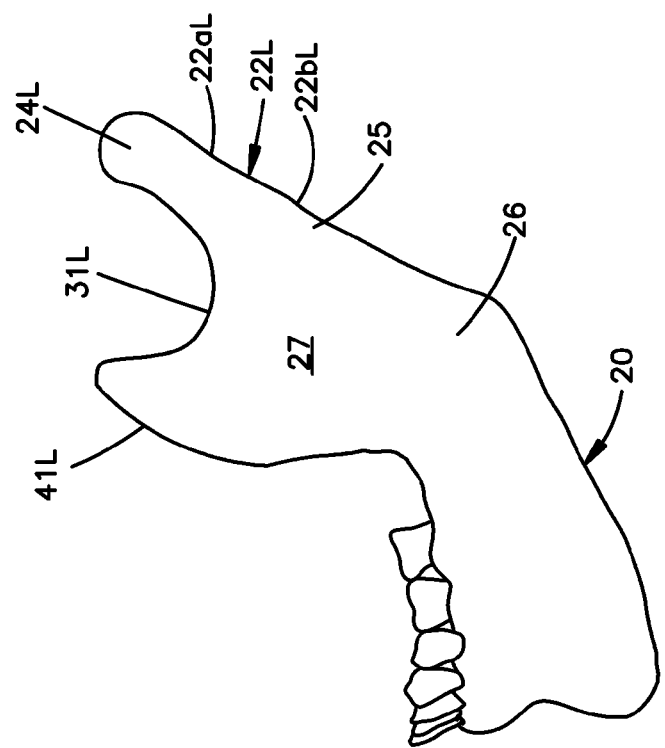
FIGS. 1A-B are perspective views of a mandible.
Figure 1A:
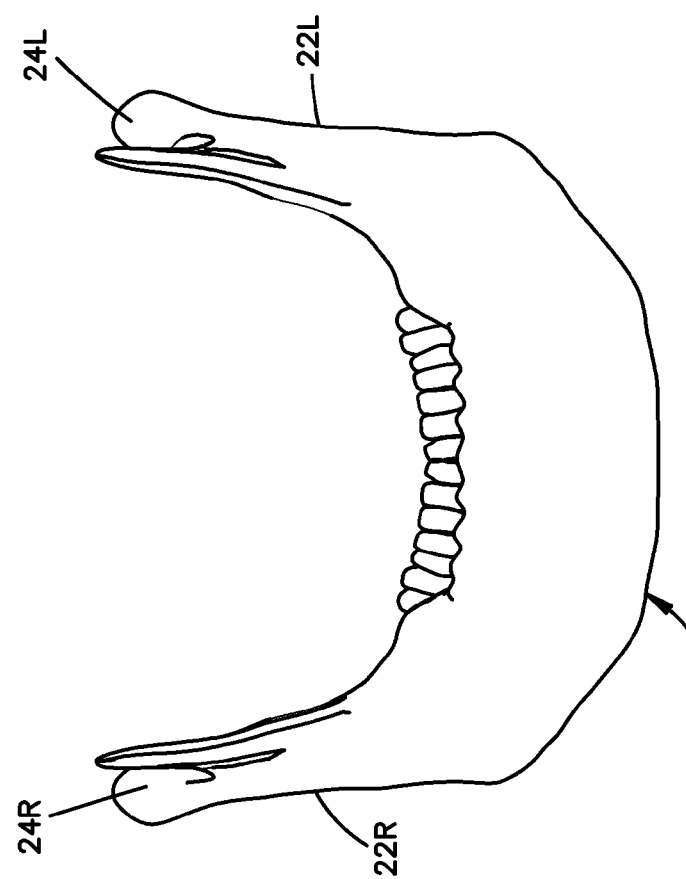

The primary leg 54 defines an inner side wall 66 and an opposing outer side wall 68 that each extend between the proximal and distal ends 58 and 60. When the fixation plate 52 is attached to an underlying mandible, the outer side wall 68 generally faces the posterior border 25 of the mandible 20, while the inner side wall 66 generally faces a mandibular region 27 that is anterior of the leg 54 (see FIGS. 1A-B). Thus, the inner side wall 66 can define a first or an anterior surface, and the outer side wall 68 can further define a second or posterior surface that is disposed posterior with respect to the first surface, which is thus disposed anterior with respect to the second surface. The inner side wall 66 and outer side wall 68 extend generally along the longitudinal axis L-L, and generally follow the contour of the apertures 70 and 72 when in alignment with the apertures. Thus, the side walls 66 and 68 define necks 76 between the apertures 70 and 72, such that the side walls 66 and 68 are closer to each other at locations at the necks 76 with respect to locations that are aligned with the apertures 70 and 72. Otherwise stated, the necks 76 define a lateral thickness (or width) that is less than the width of the leg 54 at locations laterally aligned with the apertures 70 and 72. In various embodiments, the necks 76 can define a width that is greater than, less than, or substantially equal to the diameter of the apertures 70 and 72. The necks 76 can define a lateral width of about 3 mm, though it should be appreciated that the lateral width of the necks 76 can be within the range of about 1 mm to about 5 mm, or any dimension as desired.

The leg 54 further includes a middle region 74 that extends longitudinally between the proximal and distal portions 59 and 61. As illustrated, the middle region 74 is devoid of permanent bone fastener-receiving apertures. The middle region 74 is configured to extend over a fracture when the fixation plate 52 is attached to an underlying bone, for instance the mandible 20. Otherwise stated, the middle region 74 is not configured to receive fasteners that attach to underlying bone. Rather, the proximal portion 59 of the primary leg 54 is configured to attach to a first bone segment, and the distal portion 61 of the primary leg 54 is configured to attach to a second bone segment that is separated from the first bone segment by a fracture. The side walls 66 and 68 taper laterally toward each other in the middle region 74, that is, along a distal direction from the distal-most aperture 70, and further along a proximal direction from the proximal-most aperture 72, so as to define a tapered profile 78 that defines a tapered throat 80.

The throat 80 is disposed substantially longitudinally midway between the distal-most aperture 70 and the proximal-most aperture 72, and defines the lowest width of the tapered profile 78. The throat 80 can define a width that is greater than, less than, or substantially equal to that of the necks 76. The leg 54 has a sufficiently narrow profile in the lateral dimension such that the opposing inner and outer side walls 66 and 68 are maintained within the anatomical borders of the condyle 24 when the fixation plate 52 is implanted on the mandible 20. It should be appreciated, however, that the leg 54 can define any suitable size, shape, and profile as desired to attach a pair of fragmented bone segments.

With continuing reference to FIG. 3, the auxiliary leg 56 extends from the primary leg 54, and is integral with the primary leg 54, though it can alternatively be discreetly connected to the primary leg 54 as desired. In accordance with the illustrated embodiment, the auxiliary leg 56 extends from the proximal end of the middle region 74, that is at a location distal of the distal-most aperture 70. It should be appreciated that the auxiliary leg 56 could alternatively extend from any alternative location of the primary leg 54 as desired, such as from the proximal portion 59. In the illustrated embodiment, the auxiliary leg 56 extends out from the inner side wall 66, such that the auxiliary leg 56 extends anteriorly from the primary leg 54 when the fixation plate 52 is attached to the underlying mandible.

Because the auxiliary leg 56 extends to the "right" of the primary leg 54 from a view of the first face 53, the bone fixation plate 52 is configured to be implanted in a patient's right subcondylar region 22R. It should be appreciated that the bone fixation plate 52 can also be constructed such that the auxiliary leg 56 extends to the "left" of the primary leg 54 from a view of the first face 53, such that the bone fixation plate 52 is configured to be implanted in a patients left subcondylar region 22L (see FIG. 4). In this regard, the fixation plate 52 can include a marking 99, such as "R" or "L" that indicates whether the plate 52 is to be implanted in the right subcondylar region 22R (i.e. a right-oriented bone fixation plate) or the left subcondylar region 22L (i.e. a left-oriented bone fixation plate), respectively.

The auxiliary leg 56 extends out from the primary leg 54 in a laterally forward direction, and also flares or curves away from the primary leg 54 as it extends distally. Accordingly, the auxiliary leg 56 is convex with respect to the primary leg 54, and terminates at a free distal end 56 disposed proximally with respect to the distal end 60 of the primary leg 54. Accordingly, the bone fixation plate 52 is provided in the general shape of the Greek letter lambda "λ" or the number seven "7."

The auxiliary leg 56 defines a proximal end 62, which also defines the laterally innermost end, that is affixed to the primary leg 54, and a free distal end 64 that also defines the laterally outermost end of the auxiliary leg 56. The auxiliary leg 56 is elongate along a centrally disposed axis C-C that is concave with respect to a straight line between the proximal end 62 to the distal end 64. The axis C-C is convex with respect to the primary leg 54. The central axis C-C can define a radius of curvature of about 22 mm, though it should be appreciated that the radius of curvature could be anywhere within the range of about 10 mm to about 30 mm. As will be described in more detail below, the auxiliary leg 56 is configured to generally conform in shape to the sigmoid notch 31 when the fixation plate 52 is implanted on the mandible 20.

The auxiliary leg 56 defines a line T that extends tangential to the central axis C-C at the proximal end 62 of the auxiliary leg 56. The tangential line T defines an angle θ with respect to the longitudinal axis LL at the intersection between the legs 54 and 56 of about 47°, though it should be appreciated that the angle θ could be anywhere within the range of about 30° to about 70°. It should be appreciated, of course, that the auxiliary leg 56 could define any suitable alternative shape as desired. For instance, the leg 56 could extend straight instead of curved, or could define straight segments that are angled with respect to each other. Thus, the central axis CC could define the angle θ if, for instance, the central axis C-C was linear at the intersection between the proximal end 62 and the primary leg 54. Thus, when it is said that the central axis C-C "defines" an angle with respect to the longitudinal axis L-L, the central axis C-C could define the angle directly, or via a line that extends tangential T to the central axis C-C.

The auxiliary leg 56 defines an inner side wall 82 and an opposing outer side wall 84 that each extends between the proximal and distal ends 62 and 64, respectively. The inner side wall 82 is disposed closer to the inner side wall 66 of the primary leg 54 than the outer side wall 84 and faces the inner side wall 66. The outer side wall 84 faces a direction opposite the inner side wall 82. Thus, the outer side wall 84 is configured to face the sigmoid notch 31 when the fixation plate 52 is implanted. Otherwise stated, the outer side wall 84 is disposed anterior with respect to the inner side wall 82. Accordingly, the outer side wall 84 defines an anterior-most surface of the implant body 51, and the outer side wall 68 defines a posterior-most surface of the implant body 51. Furthermore, the outer side wall 82, and in particular the auxiliary leg 56, is geometrically shaped to correspond generally to the curvature of the sigmoid notch 31 when the outer side wall 68 of the primary leg 54 is aligned with the posterior border 25 of the mandible 20.

The plate body 51 defines a proximal portion 63 of the auxiliary leg 56 adjacent to the proximal end 62, and a distal portion 65 of the auxiliary leg 56 that is disposed adjacent to the distal end 64. The auxiliary leg 56 further defines one or more bone fixation apertures 86 at the distal portion 65, such that the proximal end 62 is free of apertures. Each of the apertures 86 is configured to receive a permanent fastener 55, such as a bone screw, rivet, pin, nail, or any suitable alternative fasteners, for permanently attaching to underlying bone structure, that is for as long as the bone plate 52 is implanted. The apertures 86 can be threaded or unthreaded as desired. A pair of apertures 86 are illustrated as being disposed adjacent each other along the central axis C-C. The apertures 86 can be spaced apart along the axis C-C a distance greater than, less than, or substantially the same distance as adjacent apertures 70 and 72. The bone plate 52 may be adequately secured to the underlying bone structure without fastening all of the apertures 86. Any of the apertures 86 which are unfastened can be trimmed off from the bone plate 52 as desired by the surgeon.

The inner side wall 82 and outer side wall 84 extend generally along the central axis C-C, and generally follow the contour of the apertures 86 when in alignment with the apertures. Thus, the side walls 82 and 84 define necks 88 between the apertures 86, such that the side walls 82 and 84 are closer to each other at locations at the necks 88 with respect to locations that are aligned with the apertures 86. The necks 88 define a width W that can be less, greater than, or substantially equal to the width of the necks 76. The width W can be about 3 mm as illustrated, or anywhere within the range of about 1 mm to about 5 mm. The side walls 82 and 84 taper toward each other at a location proximal of the apertures 86, so as to define a throat 95 having a tapered profile 92.

In accordance with the illustrated embodiment, the proximal portion 63 of the auxiliary leg 56 is devoid of permanent bone-fastener receiving apertures extending transversely therethrough, such that the proximal portion 63 is configured to extend over a fracture when the fixation plate 52 is attached to an underlying bone, for instance the mandible 20. Otherwise stated, the proximal end 62 is not configured to receive any permanent bone fasteners that attach to underlying bone. Accordingly, the middle region 74 of the primary leg 54 and the proximal portion 63 of the auxiliary leg 56 define a spanning portion 90 configured to extend across a fracture site in the subcondylar region 22 when the fixation plate 52 is attached to the fractured bone segments.

Figure 4:
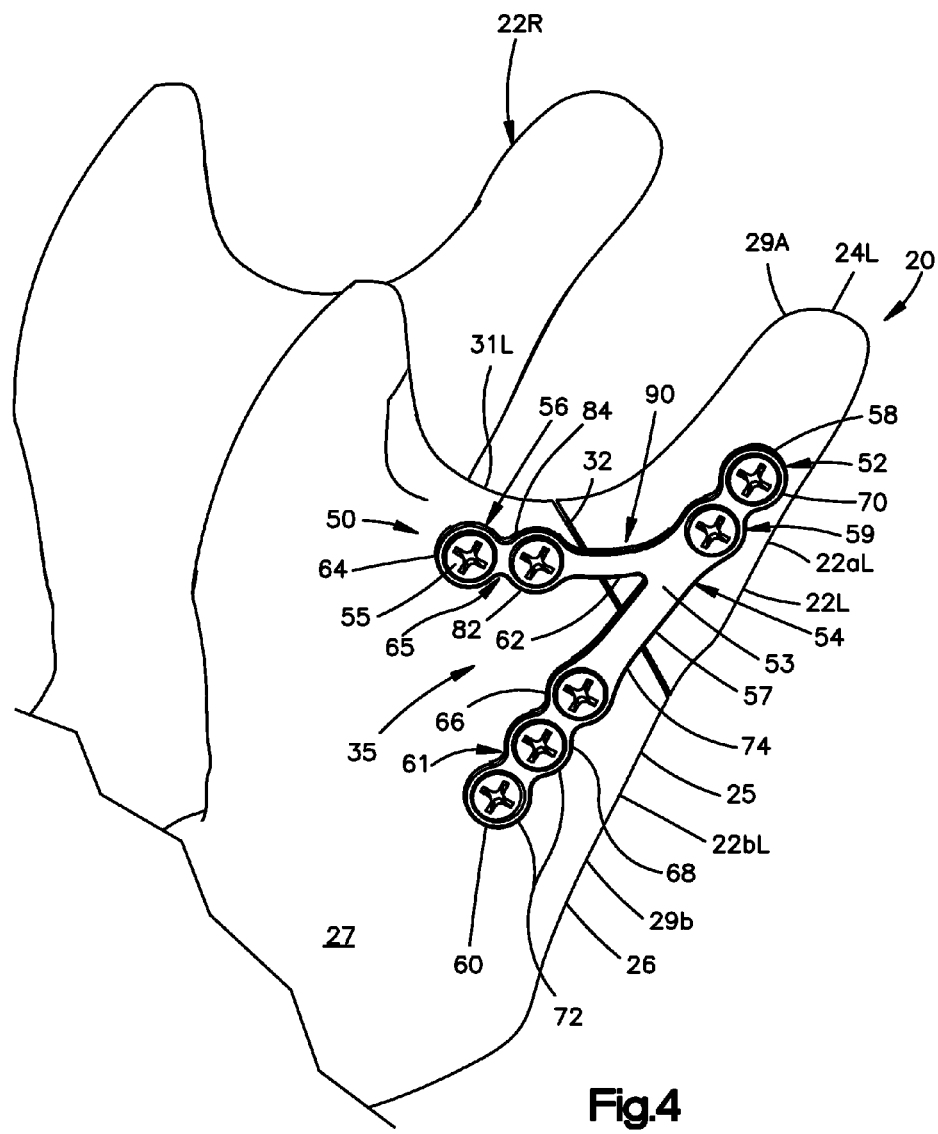
FIG. 4 is an enlarged perspective view of a bone fixation implant including the bone fixation plate of the type illustrated in FIG. 3, shown implanted onto the mandible and a plurality of bone anchors that fix the bone fixation plate to the mandible.

Referring now to FIG. 4, the mandible 20 defines a fracture site 32 at the lower condyle region 22 that separates a pair of fractured bone segments 29A and 29B. The fracture site 32 can be disposed anywhere between and including the upper subcondylar region 22a and the lower subcondylar region 22b. Accordingly, the bone segment 29A is superior to the bone segment 29B, and includes the condyle 24. The bone fixation plate 52 is constructed such that the spanning portion 90 extends over the fracture site 32, while allowing fixation of all apertures 70, 72, and 86 to the underlying mandible 20. For instance, the proximal portion 59 of the primary leg 54 is configured to overlay and attach to the condyle 24 (or bone segment 29A) when the spanning portion 90 extends across the fracture site 32, and the distal portion 61 of the primary leg 54 and the distal portion 65 of the auxiliary leg 56 are configured to overlay and attach to the inferior bone segment 29B, which can include the ramus 26. It should be further appreciated that the auxiliary leg 56 is spaced from the primary leg 54 such that the neither the fixation plate 52 nor the fasteners 55 interfere with the inferior alveolar nerve 35, which can be disposed between the primary leg 54 and the auxiliary leg 56 when the fixation plate 52 is fixed to the mandible 20.

Figure 5:
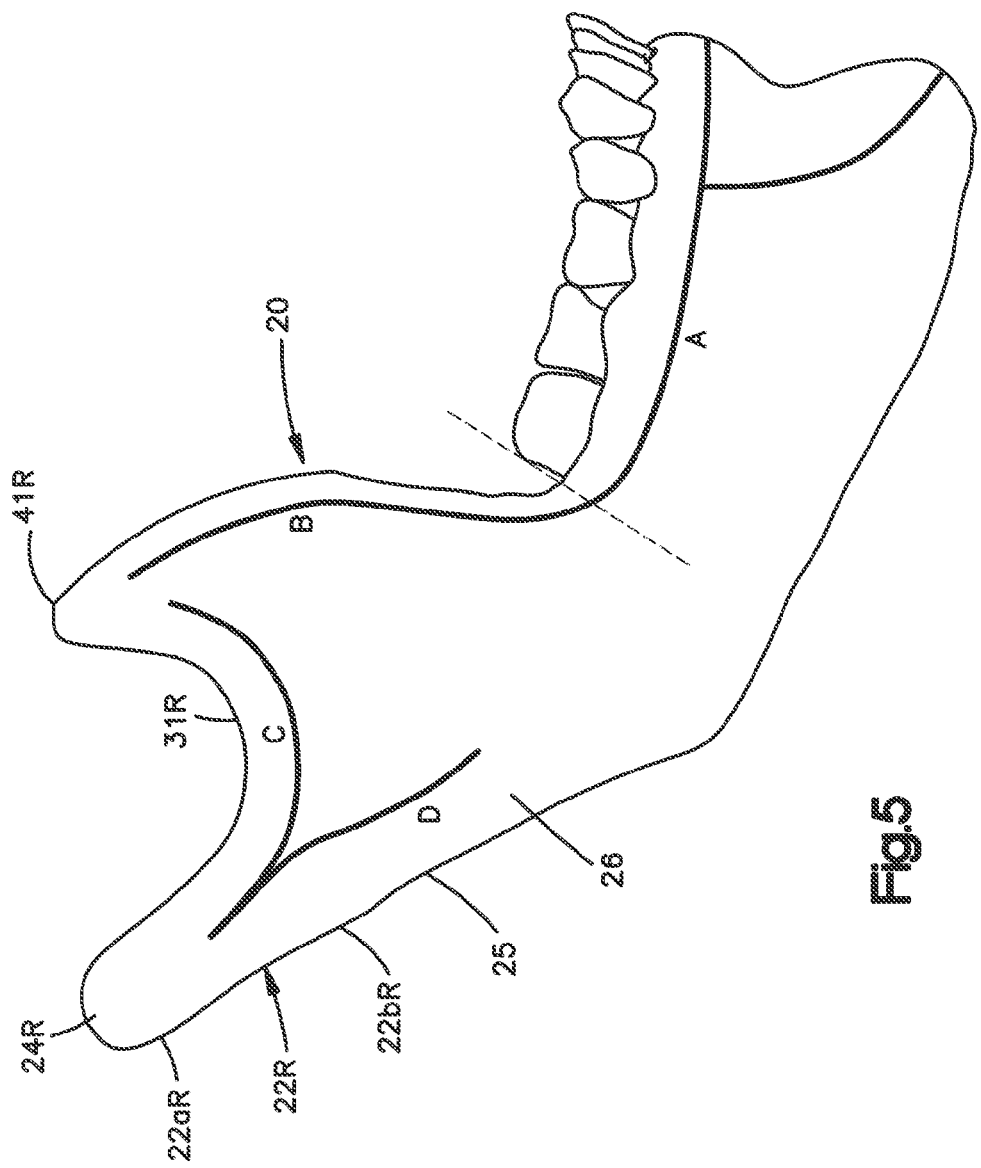
FIG. 5 is a diagram of anatomical stress lines of a mandible.

As shown in FIG. 5, without being bound by theory, it is recognized that the mandible 20 experiences primary stresses at the illustrated stress lines A, B, C, and D during anatomical function of the mandible. The stress lines C and D are capable of acting on the subcondylar region 22, and can thus most directly affect the ability of a subcondylar fracture to properly heal. Thus, referring again to FIG. 4, it should be appreciated that the primary leg 54 is configured to extend substantially along the stress line D, while the auxiliary leg 56 is configured to extend substantially along the stress line C. The fixation plate 52 is thus configured to be anatomically positioned on the mandible 20 so as to absorb the stresses applied during anatomical function of the mandible. Moreover, the auxiliary leg 56 assists in preventing twisting, in-plane bending, and out-of-plane bending of the fixation plate. Thus, the bone plate 52 can be substantially planar, and extend in a plane defined by the longitudinal L and lateral A directions.

It should be further appreciated that the geometric shape of the fixation plate 52 provides a cognitive guide that properly aligns the plate 52 on the mandible 20. For instance, the primary leg 54, and in particular the outer side wall 68 of the leg 54, is aligned with the posterior border 25 of the mandible 20 when the auxiliary leg 56, and in particular the outer side wall 84 of the auxiliary leg 56, generally follows the contour of the sigmoid notch 31. When properly positioned, the geometry of the fixation plate 52 generally corresponds to the geometry of the stress lines C and D shown in FIG. 5.

It should be appreciated that while the bone fixation plate 52 has been described in accordance with the illustrated embodiment, alternative embodiments are envisioned and intended to fall within the scope of the present disclosure. For instance, while one auxiliary leg 56 has been described, it should be appreciated that more than one auxiliary leg can extend from the primary leg 56, or an additional auxiliary leg can extend from the auxiliary leg 56. Furthermore, it should be appreciated that the size and shape of the legs 54 and 56 could differ. For instance, curved leg portions can be replaced by straight leg portions, or portions having a plurality of straight leg segments that are angularly offset with respect to each other so as to approximate e a curved profile (herein intended fall within the scope of a substantially curved shape). Furthermore, the lengths, widths, and thicknesses of the legs 54 and 56, along with the number, size, and placement of the bone fixation apertures 70, 72, and 86 could differ. Thus, the scope of the present disclosure is intended to include, but not necessarily be limited to, a bone plate having an improved approximation of the stress lines C and D with respect to conventional bone plates.

With continuing reference to FIGS. 3-4, it should be appreciated that the left-oriented bone fixation plates 52 and the right-oriented bone fixation plates are symmetrical with respect to each other, and each bone fixation plate 52 is asymmetrical. Accordingly, a kit including at least one left-oriented bone fixation plate and at least one right-oriented bone fixation plate can be provided. Furthermore, while it is envisioned that one size fixation plate 52 can be provided for the vast majority of subcondylar fractures, a kit can nevertheless include fixation plates 52 having different size and shape characteristics, and can be constructed in accordance with any embodiment as described herein.

Figure 6A:
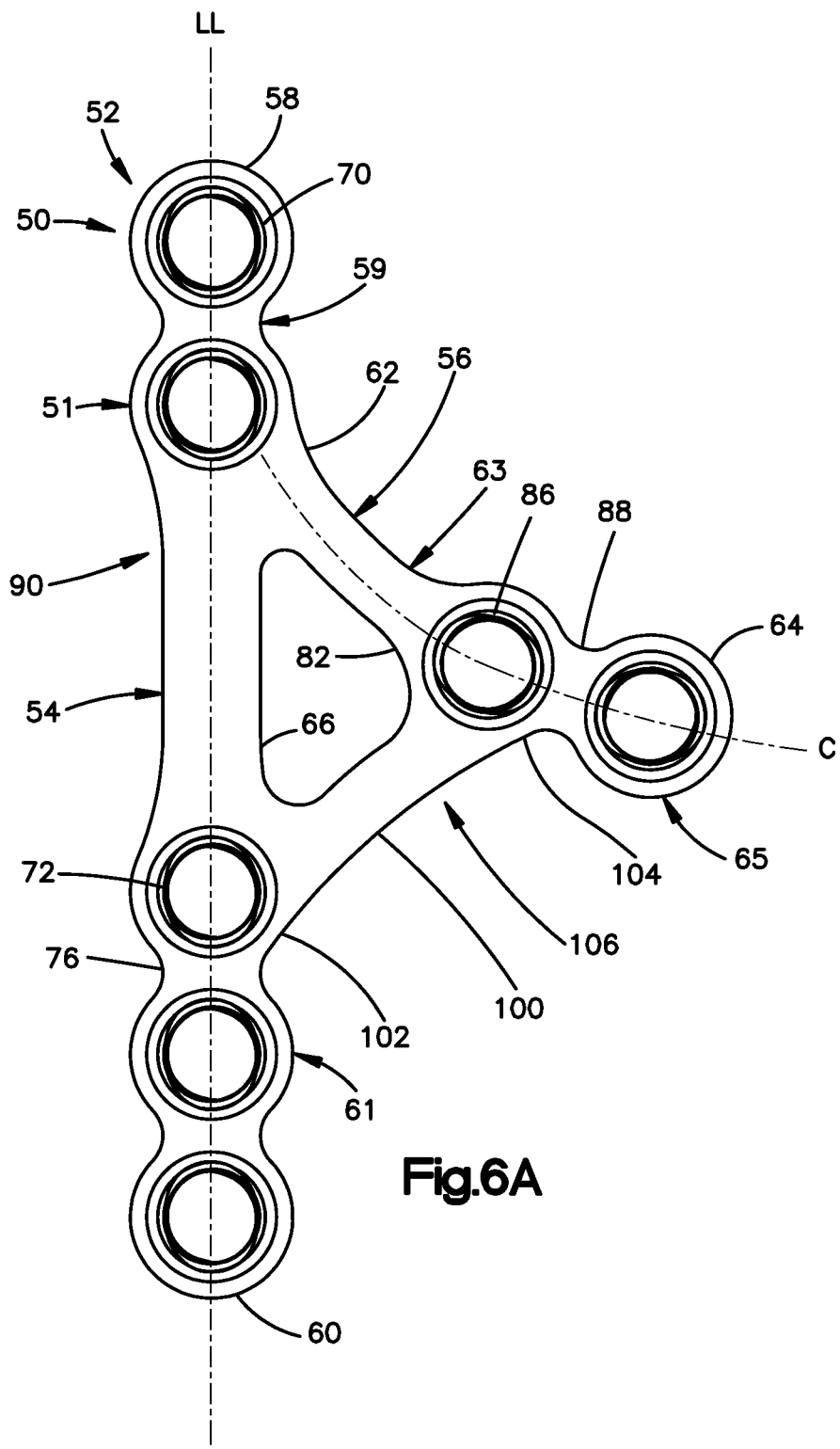
FIG. 6A is a top plan view of a subcondylar bone fixation plate constructed in accordance with an alternative embodiment.

Referring now to FIG. 6A, a bone fixation plate 52 can be constructed in accordance with an alternate embodiment. The plate 52 can define a plate body 51 that includes the primary leg 54 and the auxiliary leg 56 as described above, along with a support leg 100 connected between the primary leg 54 and the auxiliary leg 56. In particular, the support leg 100 defines a first end 102 and an opposed second end 104. The first end 102 is connected to the inner side wall 66 of the primary leg 54 and the second end 104 is connected to the inner side wall 82 of the auxiliary leg 56. In accordance with the illustrated embodiment, the support leg 100 is integral with primary and auxiliary legs 54 and 56, though the support leg can be discretely connected to one or both of the legs 54 and 56. As shown in FIG. 6A, the support leg 100 joins distal portion 61 of the primary leg 54 and the portion 65 of the auxiliary leg 56, though it should be appreciated that the positioning of the support leg 100 can vary as desired. For instance, the end 102 can be connected to the primary leg 54 anywhere along the inner side wall 66, such as at a location aligned with a fixation aperture 72 as shown, or aligned with one of the necks 76 or anywhere else along the inner side wall 66. Similarly, the second end 104 can be connected to the auxiliary leg 56 anywhere along the inner side wall 82, such as at a location aligned with a fixation aperture 86 as shown, or alternatively aligned with a neck 88 or anywhere else along the inner side wall 82.

The support leg 100 can be tapered as shown decreasing in width from the first end 102 to a middle portion 106 that is disposed between the first and second ends 102 and 104, and increasing in width from the middle portion 106 toward the second end 104. Alternately, support leg 100 can be a constant width from the first end 102 to the second end 104. The support leg 100 can extend substantially straight between the opposed outer ends 102 and 104, or can be substantially curved as desired. Furthermore, while the support leg 100 is devoid of permanent bone fastener-receiving apertures, the support leg 100 can alternatively define permanent bone fastener-receiving apertures of the type described above with respect to the primary and auxiliary legs 54 and 56.

Figure 6B:
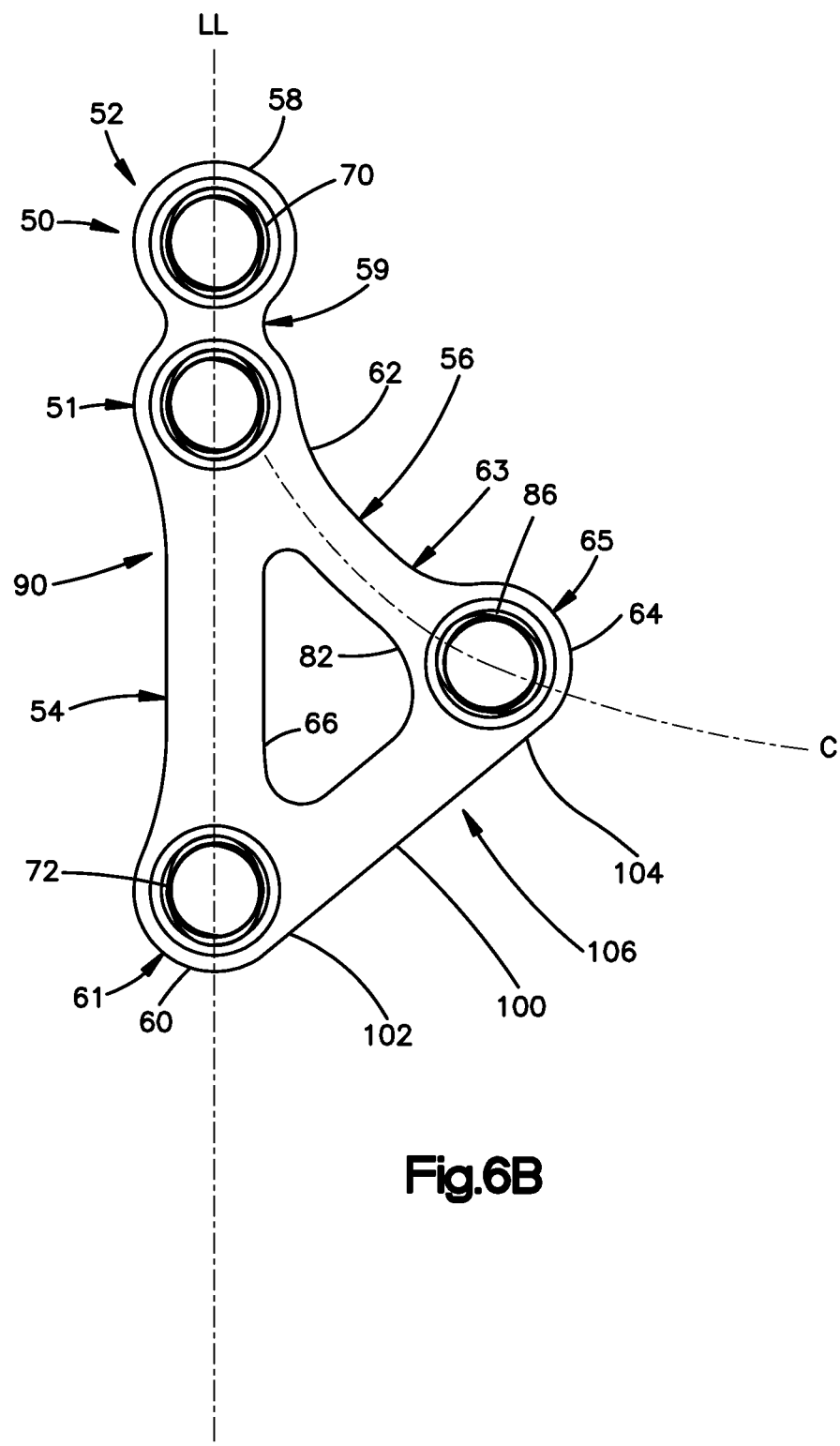
FIG. 6B is a top plan view of the subcondylar bone fixation plate as illustrated in FIG. 6A, but constructed in accordance with another alternative embodiment.

It should be appreciated that the support leg 100 adds stability to bone fixation plate 52, and can allow the bone fixation plate 52 to be attached to the underlying bone structure using a fewer number of fasteners 55 with respect to the bone fixation plate 52 that does not include the support leg 100. As a result, as illustrated in FIG. 6B, at least one or both of the distal end 60 of the primary leg 54 and the distal end 64 of the auxiliary leg 56 can be disposed at the intersection with the support leg 100, such that one or both of the distal portions 61 and 65 do not extend beyond the respective outer ends 102 and 104 of the support plate, thereby reducing the number of fixation apertures 72 and 86 and simplifying the surgical fixation procedure.

The embodiments described in connection with the illustrated embodiments have been presented by way of illustration, and the present invention is therefore not intended to be limited to the disclosed embodiments. For instance, the bone fixation plate 52 is further anatomically shaped to repair a fracture of the coronoid process 41 (see FIG. 1B) in the manner described above with respect to the subcondylar region 22. Accordingly, those skilled in the art will realize that the invention is intended to encompass all modifications and alternative arrangements included within the spirit and scope of the invention, as set forth by the appended claims.

What is claimed:

1. A method of bone fixation comprising the steps of:
orienting a mandibular bone plate in a position relative to a mandible such that: 1) a substantially straight primary leg of the mandibular bone plate is generally parallel to a portion of a posterior border of the mandible, and 2) an auxiliary leg of the mandibular bone plate that is elongate along a substantially curved central axis is generally parallel to a sigmoid notch of the mandible;
securing a portion of the primary leg to a first bone fragment of the mandible while the mandibular bone plate is in the position; and
securing a portion of the auxiliary leg to a second bone fragment of the mandible while the mandibular bone plate is in the position, wherein the second bone fragment is separated from the first bone fragment by a fracture of the mandible.

2. The method of claim 1, wherein the step of securing a portion of the primary leg includes the steps of:
aligning a hole of the mandibular bone plate that is defined by the primary leg with a portion of the first bone fragment with respect to a direction that is normal to the portion of the first bone fragment; and
inserting a bone fastener through the hole along the direction and into the first bone fragment.

3. The method of claim 2, wherein the hole is a first hole, the bone fastener is a first bone fastener, the direction is a first direction, and the step of securing a portion of the auxiliary leg includes the steps of:
aligning a second hole of the mandibular bone plate that is defined by the auxiliary leg with a portion of the second bone fragment with respect to a second direction that is normal to the portion of the second bone fragment; and
inserting a second bone fastener through the second hole along the second direction and into the second bone fragment.

4. The method of claim 3, wherein the portion of the primary leg is a first portion of the primary leg, and the method further comprises the step of:
securing a second portion of the primary leg to the second bone fragment of the mandible while the mandibular bone plate is in the position.

5. The method of claim 4, wherein the portion of the second bone fragment is a first portion of the second bone fragment, the step of securing a second portion of the primary leg includes the steps of:
aligning a third hole of the mandibular bone plate that is defined by the primary leg with a second portion of the second bone fragment with respect to a third direction that is normal to the second portion of the second bone fragment; and
inserting a third bone fastener through the third hole along the third direction and into the second bone fragment.

6. The method of claim 5, wherein the orienting step includes the step of:
aligning the primary leg with the fracture such that a third portion of the primary leg that is devoid of bone fixation holes is aligned with the fracture with respect to a direction perpendicular to a direction the first bone fragment is separated from the second bone fragment by the fracture.

7. The method of claim 1, wherein the step of securing a portion of the auxiliary leg includes the steps of:
aligning a hole of the mandibular bone plate that is defined by the auxiliary leg with a portion of the second bone fragment with respect to a direction normal to the portion of the second bone fragment; and
inserting a bone fastener through the hole along the direction and into the second bone fragment.

8. The method of claim 1, wherein the portion of the primary leg is a first portion of the primary leg, and the method further comprises the step of:
securing a second portion of the primary leg to the second bone fragment of the mandible while the mandibular bone plate is in the position.

9. The method of claim 8, wherein the step of securing a second portion of the primary leg includes the steps of:
aligning a hole of the mandibular bone plate that is defined by the primary leg with a portion of the second bone fragment with respect to a direction that is normal to the portion of the second bone fragment; and
inserting a bone fastener through the hole along the direction and into the second bone fragment.

10. The method of claim 1, wherein the orienting step includes the step of:
aligning the primary leg with the fracture such that a portion of the primary leg that is devoid of bone fixation holes is aligned with the fracture with respect to a direction perpendicular to a direction the first bone fragment is separated from the second bone fragment by the fracture.

11. A method of bone fixation comprising the steps of:
abutting a first surface of a mandibular bone plate against a mandible in a position such that: 1) a substantially straight primary leg of the mandibular bone plate is generally aligned with a stress line of the mandible with respect to a direction normal to the first surface, and 2) an auxiliary leg of the mandibular bone plate that is elongate along a substantially curved central axis is generally aligned with a second stress line of the mandible;
securing a portion of the primary leg to a first bone fragment of the mandible while the mandibular bone plate is in the position; and
securing a portion of the auxiliary leg to a second bone fragment of the mandible while the mandibular bone plate is in the position, wherein the second bone fragment is separated from the first bone fragment by a fracture of the mandible.

12. The method of claim 11, wherein the step of securing a portion of the primary leg includes the steps of:
aligning a hole of the mandibular bone plate that is defined by the primary leg with a portion of the first bone fragment with respect to a direction that is normal to the portion of the first bone fragment; and
inserting a bone fastener through the hole along the direction and into the first bone fragment.

13. The method of claim 12, wherein the hole is a first hole, the bone fastener is a first bone fastener, the direction is a first direction, and the step of securing a portion of the auxiliary leg includes the steps of:
aligning a second hole of the mandibular bone plate that is defined by the auxiliary leg with a portion of the second bone fragment with respect to a second direction that is normal to the portion of the second bone fragment; and
inserting a second bone fastener through the second hole along the second direction and into the second bone fragment.

14. The method of claim 13, wherein the portion of the primary leg is a first portion of the primary leg, and the method further comprises the step of:
 securing a second portion of the primary leg to the second bone fragment of the mandible while the mandibular bone plate is in the position.

15. The method of claim 14, wherein the portion of the second bone fragment is a first portion of the second bone fragment, the step of securing a second portion of the primary leg includes the steps of:
 aligning a third hole of the mandibular bone plate that is defined by the primary leg with a second portion of the second bone fragment with respect to a third direction that is normal to the second portion of the second bone fragment; and
 inserting a third bone fastener through the third hole along the third direction and into the second bone fragment.

16. The method of claim 15, wherein the orienting step includes the step of:
 aligning the primary leg with the fracture such that a third portion of the primary leg that is devoid of bone fixation holes is aligned with the fracture with respect to a direction perpendicular to a direction the first bone fragment is separated from the second bone fragment by the fracture.

17. The method of claim 11, wherein the step of securing a portion of the auxiliary leg includes the steps of:
 aligning a hole of the mandibular bone plate that is defined by the auxiliary leg with a portion of the second bone fragment with respect to a direction normal to the portion of the second bone fragment; and
 inserting a bone fastener through the hole along the direction and into the second bone fragment.

18. The method of claim 11, wherein the portion of the primary leg is a first portion of the primary leg, and the method further comprises the step of:
 securing a second portion of the primary leg to the second bone fragment of the mandible while the mandibular bone plate is in the position.

19. The method of claim 18, wherein the step of securing a second portion of the primary leg includes the steps of:
 aligning a hole of the mandibular bone plate that is defined by the primary leg with a portion of the second bone fragment with respect to a direction that is normal to the portion of the second bone fragment; and
 inserting a bone fastener through the hole along the direction and into the second bone fragment.

20. The method of claim 11, wherein the orienting step includes the step of:
 aligning the primary leg with the fracture such that a portion of the primary leg that is devoid of bone fixation holes is aligned with the fracture with respect to a direction perpendicular to a direction the first bone fragment is separated from the second bone fragment by the fracture.

* * * * *